(12) United States Patent
Gao et al.

(10) Patent No.: US 8,030,508 B2
(45) Date of Patent: Oct. 4, 2011

(54) POROUS ZEOLITE OF ORGANOSILICON, A METHOD FOR PREPARING THE SAME AND THE USE OF THE SAME

(75) Inventors: Huanxin Gao, Shanghai (CN); Bin Zhou, Shanghai (CN); Yilun Wei, Shanghai (CN); Hua Fang, Shanghai (CN); Ruifang Gu, Shanghai (CN); Shufang Ji, Shanghai (CN)

(73) Assignees: China Petroleum & Chemical Corporation, Beijing (CN); Shanghai Research Institute Of Petrochemical Technology Sinopec, Shanghai (CN)

( * ) Notice: Subject to any disclaimer, the term of this patent is extended or adjusted under 35 U.S.C. 154(b) by 318 days.

(21) Appl. No.: 12/377,159

(22) PCT Filed: Jul. 17, 2007

(86) PCT No.: PCT/CN2007/002177
§ 371 (c)(1),
(2), (4) Date: Mar. 9, 2009

(87) PCT Pub. No.: WO2008/019570
PCT Pub. Date: Feb. 21, 2008

(65) Prior Publication Data
US 2009/0247776 A1 Oct. 1, 2009

(30) Foreign Application Priority Data

Aug. 11, 2006 (CN) .......................... 2006 1 0029980

(51) Int. Cl.
C07F 7/02 (2006.01)
B01J 29/04 (2006.01)
C01B 39/00 (2006.01)

(52) U.S. Cl. ........ 556/173; 423/702; 423/718; 556/457; 585/457; 502/62

(58) Field of Classification Search .................. 556/173, 556/457; 423/702, 718; 585/457; 502/62
See application file for complete search history.

(56) References Cited

U.S. PATENT DOCUMENTS

| | | | |
|---|---|---|---|
| 3,702,886 | A | 11/1972 | Argauer et al. |
| 3,709,979 | A | 1/1973 | Chu et al. |
| 3,832,449 | A | 8/1974 | Rosinki et al. |
| 4,016,245 | A | 4/1977 | Plank et al. |
| 4,151,189 | A | 4/1979 | Rubin et al. |
| 4,439,409 | A | 3/1984 | Puppe et al. |
| 4,954,325 | A | 9/1990 | Rubin et al. |
| 5,235,675 | A | 8/1993 | Sudoh |
| 5,362,697 | A | 11/1994 | Fung et al. |
| 6,162,416 | A | 12/2000 | Gajda et al. |

FOREIGN PATENT DOCUMENTS

| | | |
|---|---|---|
| CN | 1266019 A | 9/2000 |
| CN | 1274616 A | 11/2000 |
| CN | 1304871 A | 7/2001 |
| JP | 2005041763 A | 2/2005 |

Primary Examiner — Porfirio Nazario Gonzalez
(74) Attorney, Agent, or Firm — Scully, Scott, Murphy & Presser, P.C.

(57) ABSTRACT

The present invention relates to an organosilicon porous zeolite, preparation of the same, and use of the same. The organosilicon porous zeolite of the invention has the following composition on molar basis: $(1/n)Al_2O_3:SiO_{(2-m/2)}:mR:xM$, wherein n=5 to 1000, m=0.001 to 1, x=0.005 to 2, R is at least one selected from the group consisting of alkyl, alkenyl and phenyl and connected to a silicon atom in the framework of the zeolite, and M is an organic amine templating agent, wherein a solid $Si^{29}$NMR spectrum of the zeolite has at least one $Si^{29}$ nuclear magnetic resonance peak in the range of from −80 to +50 ppm, and wherein a X-ray diffraction pattern of the zeolite exhibits diffraction peaks corresponding to d-spacing of 12.4±0.2, 11.0±0.3, 9.3±0.3, 6.8±0.2, 6.1±0.2, 5.5±0.2, 4.4±0.2, 4.0±0.2 and 3.4±0.1 Å. The porous zeolite can be used as an adsorbent or as a component of a catalyst for the conversion of an organic compound.

14 Claims, 1 Drawing Sheet

US 8,030,508 B2

POROUS ZEOLITE OF ORGANOSILICON, A METHOD FOR PREPARING THE SAME AND THE USE OF THE SAME

CROSS REFERENCE OF RELATED APPLICATION

The present application claims the benefit of the Chinese Patent Application No. 200610029980.3, filed on Aug. 11, 2006, which is incorporated herein by reference in their entirety and for all purposes.

FIELD OF THE INVENTION

The present invention relates to an organosilicon porous zeolite, synthesis of the same and use of the same.

BACKGROUND OF THE INVENTION

In industry, porous inorganic oxide materials are widely used as catalysts and supports of catalyst. The porous inorganic oxide materials have relatively high specific surface area and expedite channel structure, and thus are good catalytic materials and good supports of catalyst. The porous inorganic oxide materials include amorphous porous oxide materials, crystalline molecular sieve, modified layered materials, etc.

The basic framework structure of crystalline porous zeolites is based on rigid three-dimensional $TO_4$ ($SiO_4$, $AlO_4$, and the like) units, which as tetrahedrons share oxygen atoms. The change of some tetrahedrons constituting the framework, such as $AlO_4$, is balanced by the present of surface cation, such as $Na^+$ and $H^+$. Thus properties of a zeolite can be altered by cation exchange. Furthermore, there are many channels having a certain pore diameter in zeolite structure, and these channels intersect to form a three-dimensional network structure. Due to such a structure, zeolites not only exhibit good catalytic activity in many kinds of organic reaction but also have good shape selectivity to thereby achieve good reaction selectivity (see, U.S. Pat. No. 6,162,416, U.S. Pat. No. 4,954,325, and U.S. Pat. No. 5,362,697).

Synthetic crystalline porous zeolites are generally synthesized by hydrothermal methods, and typically a specific templating agent, also known as structure directing agent, is used in the synthesis of a specific zeolite. Such templating agents or structure directing agents are often nitrogen-containing organic compounds. Many zeolites and synthesis thereof have been disclosed in literatures. See, for example, U.S. Pat. No. 3,702,886 (ZSM-5), U.S. Pat. No. 4,151,189 (ZSM-5), U.S. Pat. No. 3,709,979 (ZSM-11), U.S. Pat. No. 3,832,449 (ZSM-12), U.S. Pat. No. 4,016,245 (ZSM-35), Zeolite, 1991, Vol 11, p 202 (Beta zeolite), U.S. Pat. No. 4,439,409 (PSH-3), U.S. Pat. No. 4,954,325 (MCM-22), U.S. Pat. No. 5,362,697 (MCM-56), U.S. Pat. No. 5,236,575 (MCM-49), Nature, 1998, Vol 396, p 353 (ITQ-2). The above crystalline zeolites have frameworks consisting essentially of inorganic silicon oxide and inorganic aluminum oxide. A zeolite having an organosilicon-containing framework and its synthesis have not been reported.

SUMMARY OF THE INVENTION

An object of the invention is to provide a novel organosilicon porous zeolite, of which framework contains silicon atoms carrying at least one organic group selected from the group consisting of alkyl, alkenyl and phenyl.

Another object of the invention is to provide a process for synthesizing the novel organosilicon porous zeolite.

Still another object of the invention is to provide use of the organosilicon porous zeolite.

DETAILED DESCRIPTION OF THE PREFERRED EMBODIMENTS

Figure 1:
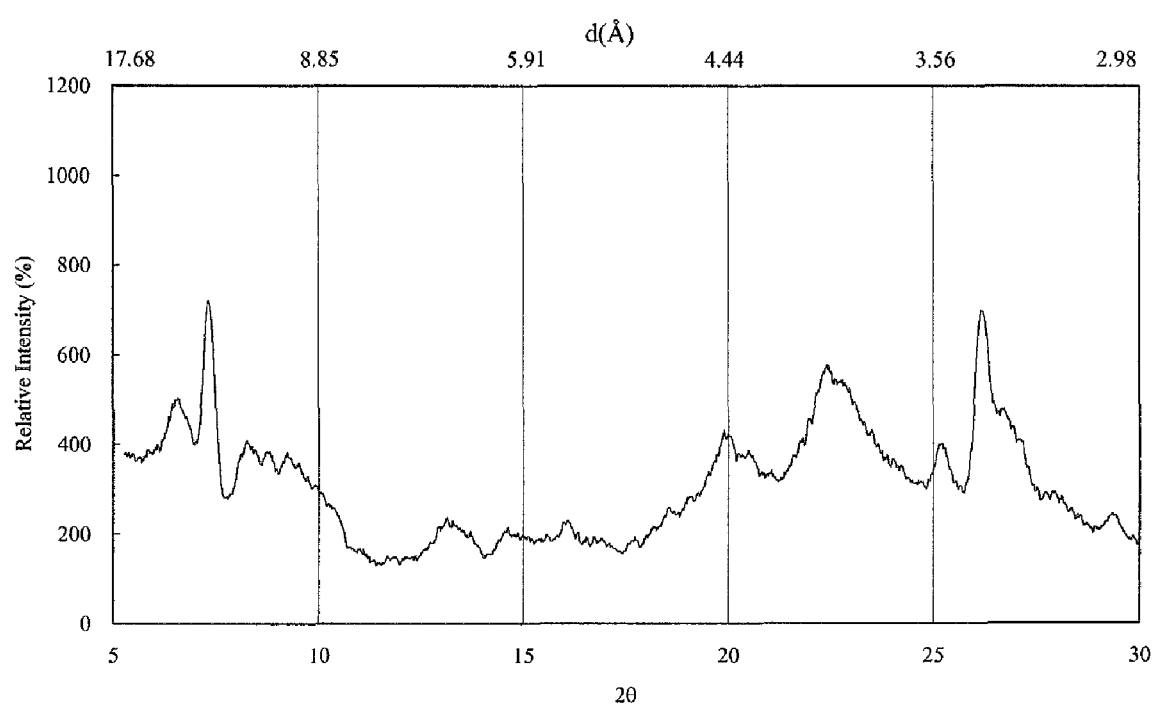
FIG. 1 is XRD pattern of the zeolite obtained in Example 1.

In the first aspect, the present invention provides an organosilicon porous zeolite having the following composition on molar basis: $(1/n)Al_2O_3:SiO_{(2-m/2)}:mR:xM$, wherein n=5 to 1000, m=0.001 to 1, x=0.005 to 2, R is at least one selected from the group consisting of alkyl, alkenyl and phenyl and connected to a silicon atom in the framework of the zeolite, and M is an organic amine templating agent.

Solid $^{29}SiNMR$ spectrum of the zeolite has at least one $Si^{29}$ nuclear magnetic resonance peak in the range of from −80 to +50 ppm.

X-ray diffraction pattern of the zeolite exhibits diffraction peaks corresponding to d-spacing of 12.4±0.2, 11.0±0.3, 9.3±0.3, 6.8±0.2, 6.1±0.2, 5.5±0.2, 4.4±0.2, 4.0±0.2 and 3.4±0.1 Å.

As used herein, the term "organosilicon porous zeolite" intends to means a zeolite which as synthesized contains, in its framework structure, silicon atoms having at least one organic substituent, in particular at least one selected from the group consisting of alkyl, alkenyl and phenyl.

In a preferred embodiment, n is in a range of from 10 to 250, m is in a range of from 0.01 to 0.8, and x is in a range of from 0.01 to 1. In a more preferred embodiment, n is in a range of from 10 to 150, m is in a range of from 0.02 to 0.5, and x is in a range of from 0.02 to 0.5.

In a preferred embodiment, the R is at least one selected from the group consisting of $C_1$-$C_8$ alkyl, $C_2$-$C_{10}$ alkenyl and phenyl. In a more preferred embodiment, the R is at least one selected from the group consisting of methyl, ethyl, vinyl and phenyl.

The organosilicon porous zeolite according to the invention is designated as SHY-4.

In the second aspect, the present invention provides a process for synthesizing the organosilicon porous zeolite according to the invention, comprising:

a) mixing a source of organic silicon, a source of inorganic silicon, an aluminum source, an alkali, an organic amine templating agent and water to form a reaction mixture, the reaction mixture having a composition in terms of molar ratios falling within the following ranges: $SiO_2/Al_2O_3$=5 to 1000, the source of organic silicon/$SiO_2$=0.001 to 1, $OH^-/SiO_2$=0.01 to 5.0, $H_2O/SiO_2$=5 to 100, and the organic amine/$SiO_2$=0.01 to 2.0, wherein $SiO_2$ represents the source of inorganic silicon in terms of $SiO_2$; and b) allowing the reaction mixture to react at a temperature of from 90 to 200° C. for 1 to 100 hours to form a crystalline product, and c) recovering the crystalline product obtained from step b), washing it with water and drying, to give the organosilicon porous zeolite.

Any source of $SiO_2$ commonly used in the synthesis of zeolites can be used as the source of inorganic silicon in the process of the invention. The source of inorganic silicon useful in the process of the invention is preferably at least one selected from the group consisting of silica sols, solid silica, silica gels, silicic acid esters, diatomite and water glass.

The source of organic silicon useful in the process of the invention may be at least one selected from the group consisting of halosilanes, silazanes and alkoxy silanes. Preferred examples of the halosilanes include, but are not limited to, trimethylsilyl chloride, dimethylsilyl dichloride, triethylsilyl chloride, diethylsilyl dichloride, dimethylsilyl monochloride monobromide, ethyldimethylsilyl chloride, butyldimethylsilyl chloride, dimethylphenylsilyl chloride, dimethylisopropylsilyl chloride, tert-butyldimethylsilyl chloride, dimethyloctadecylsilyl chloride, methyl phenyl vinylsilyl chloride, vinylsilyl trichloride, divinylsilyl dichloride and diphenylsilyl dichloride. Preferred examples of the silazanes include, but are not limited to, hexamethyldisilazane, heptamethyldisilazane, tetramethyldisilazane, tetramethyl divinyl disilazane, and tetramethyl diphenyl disilazane. Preferred examples of the alkoxy silanes include, but are not limited to, trimethylethoxysilane, dimethyldiethoxysilane, trimethylmethoxysilane, dimethyldimethyoxy silane, phenyltrimethoxysilane, and diphenyldiethoxysilane.

Any aluminum source commonly used in the synthesis of zeolites can be used in the process of the invention. The aluminum source useful in the process of the invention is preferably at least one selected from the group consisting of sodium aluminate, sodium metaaluminate, aluminum sulfate, aluminum nitrate, aluminum trichloride, aluminum hydroxide, aluminum oxide, kaolin and montmorillonite.

The alkali useful in the process of the invention is an inorganic alkali, and preferably at least one selected from the group consisting of lithium hydroxide, sodium hydroxide, potassium hydroxide, rubidium hydroxide, and cesium hydroxide.

The organic amine templating agent is preferably at least one selected from the group consisting of ethylenediamine, hexamethylenediamine, cyclohexylamine, hexamethylene imine, heptamethylene imine, pyridine, hexahydropyridine, butylamine, hexylamine, octylamine, quinamine, dodecylamine, hexadecylamine, and octadecylamine.

In a preferred embodiment, the reaction mixture has a composition in terms of molar ratios falling within the following ranges: $SiO_2/Al_2O_3$=10 to 250, the source of organic silicon/$SiO_2$=0.005 to 0.5, $OH^-/SiO_2$=0.05 to 1.0, $H_2O/SiO_2$=10 to 80, and the organic amine/$SiO_2$=0.05 to 1.0, wherein $SiO_2$ represents the source of inorganic silicon in terms of $SiO_2$.

In a preferred embodiment, the reaction temperature for crystallization is in a range of from 100 to 180° C., and reaction time for crystallization is in a range of from 2 to 60 hours.

In a preferred embodiment, the reaction mixture is aged at a temperature of from 10 to 80° C. for 2 to 100 hours prior to the crystallization reaction.

In the third aspect, the present invention provides a use of the organosilicon porous zeolite as an adsorbent or as a component of a catalyst for the conversion of an organic compound.

The organosilicon porous zeolite according to the invention can be used as an adsorbent, for example, for separating at least one component from a multiple-component mixture in gas phase or liquid phase. Thus, in an embodiment, the invention provides a separation process, comprising contacting a gaseous and/or liquid mixture with the organosilicon porous zeolite according to the invention, to allow the organosilicon porous zeolite to selectively adsorb at least one component of the mixture so as to separate partially or almost completely the at least one component from the mixture.

The organosilicon porous zeolite according to the invention can be used in a process for the conversion of an organic compound. For example, a catalyst comprising the organosilicon porous zeolite according to the invention can be used in liquid phase alkylation reaction of benzene with propylene, to produce isopropyl benzene. Thus, in an embodiment, the invention provides a process for preparing isopropyl benzene, comprising performing liquid phase alkylation reaction of benzene and propylene in the presence of a catalyst comprising the organosilicon porous zeolite according to the invention.

By adjusting relative amounts of the components in the reaction mixture and controlling the crystallization process, the present inventors have synthesized a porous zeolite having a specific channel structure and containing organic silicon in its framework and achieved good technical effect.

EXAMPLES

The following examples are given for further illustrating the invention, but do not make limitation to the invention in any way.

Example 1

6.1 g of sodium aluminate ($Al_2O_3$ content=42.0 wt %) and 1.0 g of sodium hydroxide were added into 288 g of water, and the mixture was stirred to dissolve the solids. Then to the mixture were successively added 34.0 g of hexahydropyridine, 60 g of solid silica and 5.5 g of trimethylsilyl chloride with stirring, and thus the reactants had molar ratios as follows:

$SiO_2/Al_2O_3$=40,
$NaOH/SiO_2$=0.025,
trimethylsilyl chloride/$SiO_2$=0.05,
hexahydropyridine/$SiO_2$=0.50, and
$H_2O/SiO_2$=16.

After stirred homogeneously, the reaction mixture was charged into a stainless steel reactor and allowed to crystallize at 135° C. for 50 hours with stirring. Then the reaction mixture was discharged and filtered, and the filter cake was washed with water and then dried to give a product. The product was found to have a molar ratio of $SiO_2/Al_2O_3$ of 42.1.

Solid $Si^{29}$NMR spectrum was measured on a sample of the dried product, and the $Si^{29}$NMR spectrum exhibited a nuclear magnetic resonance peak at 15.1 ppm. The X-ray diffraction data of the product are shown in the Table 1 below.

TABLE 1

| d-spacing (Å) | 2θ | I/I$_o$ |
| --- | --- | --- |
| 12.36 | 7.15 | 100 |
| 10.98 | 8.05 | 42 |
| 9.31 | 9.50 | 23 |
| 6.86 | 12.91 | 26 |
| 6.15 | 14.40 | 21 |
| 5.54 | 16.00 | 19 |
| 4.46 | 19.91 | 39 |
| 3.99 | 22.28 | 50 |
| 3.40 | 26.21 | 86 |

Example 2

8.0 g of sodium aluminate ($Al_2O_3$ content=42.0 wt %) and 4.0 g of sodium hydroxide were added into 360 g of water, and the mixture was stirred to dissolve the solids. Then to the mixture were successively added 34.0 g of hexahydropyridine, 150 g of silica sol (SiO$_2$ content=40 wt %) and 3.9 g of dimethylsilyl dichloride with stirring, and thus the reactants had molar ratios as follows:

SiO$_2$/Al$_2$O$_3$=30,
NaOH/SiO$_2$=0.05,
dimethylsilyl dichloride/SiO$_2$=0.03,
hexahydropyridine/SiO$_2$=0.40, and
H$_2$O/SiO$_2$=20.

After stirred homogeneously, the reaction mixture was charged into a stainless steel reactor and allowed to crystallize at 150° C. for 55 hours with stirring. Then the reaction mixture was discharged and filtered, and the filter cake was washed with water and then dried to give a product. The product was found to have a molar ratio of SiO$_2$/Al$_2$O$_3$ of 28.6.

Solid Si$^{29}$NMR spectrum was measured on a sample of the dried product, and the Si$^{29}$NMR spectrum exhibited a nuclear magnetic resonance peak at −18.4 ppm. The X-ray diffraction data of the product are shown in the Table 2 below.

TABLE 2

| d-spacing (Å) | 2θ | I/I$_o$ |
|---|---|---|
| 12.36 | 7.15 | 100 |
| 10.98 | 8.05 | 45 |
| 9.31 | 9.50 | 25 |
| 6.86 | 12.91 | 21 |
| 6.15 | 14.40 | 25 |
| 5.54 | 16.00 | 17 |
| 4.46 | 19.91 | 38 |
| 3.99 | 22.28 | 53 |
| 3.40 | 26.21 | 74 |

Example 3

3.0 g of aluminum oxide and 16.0 g of sodium hydroxide were added into 450 g of water, and the mixture was stirred to dissolve the solids. Then to the mixture were successively added 34.7 g of hexamethylene imine, 60 g of solid silica and 5.9 g of dimethyldiethoxysilane with stirring, and thus the reactants had molar ratios as follows:

SiO$_2$/Al$_2$O$_3$=30,
NaOH/SiO$_2$=0.2,
dimethyldiethoxysilane/SiO$_2$=0.04,
hexamethylene imine/SiO$_2$=0.35, and
H$_2$O/SiO$_2$=25.

After stirred homogeneously, the reaction mixture was charged into a stainless steel reactor and allowed to crystallize at 145° C. for 70 hours with stirring. Then the reaction mixture was discharged and filtered, and the filter cake was washed with water and then dried to give a product. The product was found to have a molar ratio of SiO$_2$/Al$_2$O$_3$ of 30.1.

Solid Si$^{29}$NMR spectrum was measured on a sample of the dried product, and the Si$^{29}$NMR spectrum exhibited a nuclear magnetic resonance peak at −19.1 ppm. The X-ray diffraction data of the product are shown in the Table 3 below.

TABLE 3

| d-spacing (Å) | 2θ | I/I$_o$ |
|---|---|---|
| 12.31 | 7.18 | 100 |
| 11.12 | 7.95 | 36 |
| 9.25 | 9.56 | 37 |
| 6.86 | 12.91 | 18 |
| 6.15 | 14.40 | 15 |

TABLE 3-continued

| d-spacing (Å) | 2θ | I/I$_o$ |
|---|---|---|
| 5.51 | 16.09 | 13 |
| 4.46 | 19.91 | 29 |
| 3.97 | 22.40 | 36 |
| 3.41 | 26.14 | 78 |

Example 4

16.1 g of sodium aluminate (Al$_2$O$_3$ content=42.0 wt %) and 2.0 g of sodium hydroxide were added into 540 g of water, and the mixture was stirred to dissolve the solids. Then to the mixture were successively added 30 g of hexamethylene imine, 60 g of solid silica and 3.2 g of hexamethyldisilazane with stirring, and thus the reactants had molar ratios as follows:

SiO$_2$/Al$_2$O$_3$=15,
NaOH/SiO$_2$=0.05,
hexamethyldisilazane/SiO$_2$=0.04,
hexamethylene imine/SiO$_2$=0.3, and
H$_2$O/SiO$_2$=30.

After stirred homogeneously, the reaction mixture was charged into a stainless steel reactor and allowed to crystallize at 145° C. for 38 hours with stirring. Then the reaction mixture was discharged and filtered, and the filter cake was washed with water and then dried to give a product. The product was found to have a molar ratio of SiO$_2$/Al$_2$O$_3$ of 17.5.

Solid Si$^{29}$NMR spectrum was measured on a sample of the dried product, and the Si$^{29}$NMR spectrum exhibited a nuclear magnetic resonance peak at 15.8 ppm. The X-ray diffraction data of the product are shown in the Table 4 below.

TABLE 4

| d-spacing (Å) | 2θ | I/I$_o$ |
|---|---|---|
| 12.41 | 7.12 | 100 |
| 11.00 | 8.04 | 37 |
| 9.31 | 9.50 | 23 |
| 6.90 | 12.83 | 25 |
| 6.15 | 14.40 | 18 |
| 5.54 | 16.00 | 9 |
| 4.46 | 19.91 | 41 |
| 4.00 | 22.23 | 63 |
| 3.39 | 26.29 | 89 |

Example 5

3.5 g of sodium aluminate (Al$_2$O$_3$ content=42.0 wt %) and 8.0 g of sodium hydroxide were added into 540 g of water, and the mixture was stirred to dissolve the solids. Then to the mixture were successively added 30 g of hexamethylene imine, 60 g of solid silica and 8.0 g of hexamethyldisiloxane with stirring, and thus the reactants had molar ratios as follows:

SiO$_2$/Al$_2$O$_3$=70,
NaOH/SiO$_2$=0.2,
hexamethyldisiloxane/SiO$_2$=0.05,
hexamethylene imine/SiO$_2$=0.3, and
H$_2$O/SiO$_2$=30.

After stirred homogeneously, the reaction mixture was charged into a stainless steel reactor and allowed to crystallize at 135° C. for 35 hours with stirring. Then the reaction mixture was discharged and filtered, and the filter cake was washed with water and then dried to give a product. The product was found to have a molar ratio of $SiO_2/Al_2O_3$ of 68.5.

Solid $Si^{29}$NMR spectrum was measured on a sample of the dried product, and the $Si^{29}$NMR spectrum exhibited a nuclear magnetic resonance peak at 16.8 ppm. The X-ray diffraction data of the product are shown in the Table 5 below.

TABLE 5

| d-spacing (Å) | 2θ | I/I$_o$ |
|---|---|---|
| 12.39 | 7.14 | 100 |
| 10.96 | 8.07 | 48 |
| 9.28 | 9.53 | 21 |
| 6.90 | 12.83 | 24 |
| 6.12 | 14.47 | 15 |
| 5.56 | 15.94 | 17 |
| 4.46 | 19.91 | 39 |
| 4.00 | 22.23 | 57 |
| 3.40 | 26.21 | 79 |

Example 6

2.4 g of sodium aluminate ($Al_2O_3$ content=42.0 wt %) and 40 g of sodium hydroxide were added into 900 g of water, and the mixture was stirred to dissolve the solids. Then to the mixture were successively added 20 g of hexamethylene imine, 60 g of solid silica and 48.5 g of divinylsilyl dichloride with stirring, and thus the reactants had molar ratios as follows:

$SiO_2/Al_2O_3$=100,
$NaOH/SiO_2$=1.0,
divinylsilyl dichloride/$SiO_2$=0.3,
hexamethylene imine/$SiO_2$=0.2, and
$H_2O/SiO_2$=50.

After stirred homogeneously, the reaction mixture was charged into a stainless steel reactor and allowed to crystallize at 135° C. for 35 hours with stirring. Then the reaction mixture was discharged and filtered, and the filter cake was washed with water and then dried to give a product. The product was found to have a molar ratio of $SiO_2/Al_2O_3$ of 105.3.

Solid $Si^{29}$NMR spectrum was measured on a sample of the dried product, and the $Si^{29}$NMR spectrum exhibited a nuclear magnetic resonance peak at −15.5 ppm. The X-ray diffraction data of the product are shown in the Table 6 below.

TABLE 6

| d-spacing (Å) | 2θ | I/I$_o$ |
|---|---|---|
| 12.41 | 7.12 | 100 |
| 10.95 | 8.08 | 57 |
| 9.29 | 9.52 | 36 |
| 6.91 | 12.81 | 23 |
| 6.12 | 14.47 | 19 |
| 5.55 | 15.97 | 25 |
| 4.46 | 19.91 | 43 |
| 4.02 | 22.11 | 58 |
| 3.40 | 26.21 | 81 |

Example 7

1.6 g of sodium aluminate ($Al_2O_3$ content=42.0 wt %) and 24 g of sodium hydroxide were added into 720 g of water, and the mixture was stirred to dissolve the solids. Then to the mixture were successively added 50 g of hexamethylene imine, 60 g of solid silica and 19.8 g of phenyltrimethoxysilane with stirring, and thus the reactants had molar ratios as follows:

$SiO_2/Al_2O_3$=150,
$NaOH/SiO_2$=0.6,
phenyltrimethoxysilane/$SiO_2$=0.1,
hexamethylene imine/$SiO_2$=0.5, and
$H_2O/SiO_2$=40.

After stirred homogeneously, the reaction mixture was charged into a stainless steel reactor and allowed to crystallize at 135° C. for 35 hours with stirring. Then the reaction mixture was discharged and filtered, and the filter cake was washed with water and then dried to give a product. The product was found to have a molar ratio of $SiO_2/Al_2O_3$ of 142.0.

Solid $Si^{29}$NMR spectrum was measured on a sample of the dried product, and the $Si^{29}$NMR spectrum exhibited a nuclear magnetic resonance peak at −45.1 ppm. The X-ray diffraction data of the product are shown in the Table 7 below.

TABLE 7

| d-spacing (Å) | 2θ | I/I$_o$ |
|---|---|---|
| 12.43 | 7.11 | 100 |
| 10.94 | 8.08 | 57 |
| 9.29 | 9.52 | 36 |
| 6.92 | 12.79 | 23 |
| 6.12 | 14.47 | 19 |
| 5.53 | 16.03 | 25 |
| 4.46 | 19.91 | 43 |
| 4.01 | 22.17 | 58 |
| 3.39 | 26.29 | 81 |

Example 8

3.5 g of sodium aluminate ($Al_2O_3$ content=42.0 wt %) and 8.0 g of sodium hydroxide were added into 540 g of water, and the mixture was stirred to dissolve the solids. Then to the mixture were successively added 30 g of hexamethylene imine, 60 g of solid silica and 1.6 g of hexamethyldisiloxane with stirring, and thus the reactants had molar ratios as follows:

$SiO_2/Al_2O_3$=70,
$NaOH/SiO_2$=0.2,
hexamethyldisiloxane/$SiO_2$=0.01,
hexamethylene imine/$SiO_2$=0.3, and
$H_2O/SiO_2$=30.

After stirred homogeneously, the reaction mixture was charged into a stainless steel reactor and allowed to crystallize at 135° C. for 38 hours with stirring. Then the reaction mixture was discharged and filtered, and the filter cake was washed with water and then dried to give a product. The product was found to have a molar ratio of $SiO_2/Al_2O_3$ of 68.0.

Solid $Si^{29}$NMR spectrum was measured on a sample of the dried product, and the $Si^{29}$NMR spectrum exhibited a nuclear magnetic resonance peak at 16.3 ppm. The X-ray diffraction data of the product are shown in the Table 8 below.

TABLE 8

| d-spacing (Å) | 2θ | I/I$_o$ |
|---|---|---|
| 12.37 | 7.15 | 100 |
| 10.96 | 8.07 | 48 |
| 9.26 | 9.55 | 21 |
| 6.91 | 12.81 | 24 |

TABLE 8-continued

| d-spacing (Å) | 2θ | I/I$_o$ |
|---|---|---|
| 6.12 | 14.47 | 15 |
| 5.57 | 15.91 | 17 |
| 4.48 | 19.82 | 39 |
| 4.02 | 22.11 | 57 |
| 3.46 | 25.75 | 79 |

Example 9

50 g of the powdery product as synthesized in Example 1 was exchanged with 150 ml of 1M aqueous solution of ammonium nitrate for four times, and then the solids were filtered out and dried. Then the dried solids were completely mixed with 20 g of aluminum oxide, and then 120 g of 5 wt % nitric acid was added thereto. The resultant mixture was kneaded and then extruded to form bars with size being φ1.6×2 mm. Then the extrudates were dried at 120° C., and then calcined at 520° C. for 6 hours, to form a desired catalyst.

Liquid phase alkylation reaction between propylene and benzene:

1.0 g of the catalyst as prepared above was loaded in a fixed bed reactor, and then a mixed feed consisting of propylene and benzene was introduced into the reactor. The reaction conditions were as follows: WHSV of propylene=6.0 h$^{-1}$, the molar ratio of benzene to propylene=2.0, reaction temperature=165° C., and reaction pressure=3.0 MPa. The reactor was continuously operated for 6 days. It was found that conversion of propylene was 98%, and the effluent contained 0.4 wt % of propylene, 43.8 wt % of benzene, 46.6 wt % of isopropylbenzene, 8.0 wt % of diisopropylbenzene, 0.5 wt % of triisopropylbenzene, and 260 ppm by weight of n-propylbenzene.

Comparative Example 1

6.1 g of sodium aluminate (Al$_2$O$_3$ content=42.0 wt %) and 3.2 g of sodium hydroxide were added into 288 g of water, and the mixture was stirred to dissolve the solids. Then to the mixture were successively added 34.0 g of hexahydropyridine and 60 g of solid silica with stirring, and thus the reactants had molar ratios as follows:

SiO$_2$/Al$_2$O$_3$=40,
NaOH/SiO$_2$=0.08,
hexahydropyridine/SiO$_2$=0.50, and
H$_2$O/SiO$_2$=16.

After stirred homogeneously, the reaction mixture was charged into a stainless steel reactor and allowed to crystallize at 150° C. for 45 hours with stirring. Then the reaction mixture was discharged and filtered, and the filter cake was washed with water and then dried to give a product. The product was found to have a molar ratio of SiO$_2$/Al$_2$O$_3$ of 42.8.

Solid Si$^{29}$NMR spectrum was measured on a sample of the dried product, and the Si$^{29}$NMR spectrum did not exhibit a nuclear magnetic resonance peak in the range of from 50 to −80 ppm. The X-ray diffraction data of the product are shown in the Table 9 below.

TABLE 9

| d-spacing (Å) | 2θ | I/I$_o$ |
|---|---|---|
| 13.66 | 6.47 | 59 |
| 12.51 | 7.065 | 83 |

TABLE 9-continued

| d-spacing (Å) | 2θ | I/I$_o$ |
|---|---|---|
| 11.29 | 7.83 | 47 |
| 9.23 | 9.58 | 40 |
| 6.92 | 12.80 | 24 |
| 6.18 | 14.33 | 16 |
| 5.65 | 15.70 | 15 |
| 4.44 | 20.00 | 48 |
| 3.98 | 22.35 | 59 |
| 3.54 | 25.19 | 42 |
| 3.40 | 26.21 | 100 |
| 3.31 | 26.92 | 53 |

Comparative Example 2

50 g of the powdery product as synthesized in Comparative Example 1 was exchanged with 150 ml of 1M aqueous solution of ammonium nitrate for four times, and then the solids were filtered out and dried. Then the dried solids were completely mixed with 20 g of aluminum oxide, and then 120 g of 5 wt % nitric acid was added thereto. The resultant mixture was kneaded and then extruded to form bars with size being φ1.6×2 mm. Then the extrudates were dried at 120° C., and then calcined at 520° C. for 6 hours, to form a desired catalyst.

Liquid phase alkylation reaction between propylene and benzene:

1.0 g of the catalyst as prepared above was loaded in a fixed bed reactor, and then a mixed feed consisting of propylene and benzene was introduced into the reactor. The reaction conditions were as follows: WHSV of propylene=2.0 h$^{-1}$, the molar ratio of benzene to propylene=2.0, reaction temperature=155° C., and reaction pressure=3.0 MPa. The reactor was continuously operated for 6 days. It was found that conversion of propylene was 97.5%, and the effluent contained 0.5 wt % of propylene, 43.9 wt % of benzene, 46.3 wt % of isopropylbenzene, 8.1 wt % of diisopropylbenzene, 0.5 wt % of triisopropylbenzene, and 255 ppm by weight of n-propylbenzene.

The patents, patent applications, non-patent literatures and testing methods cited in the specification are incorporated herein by reference.

While the invention has been described with reference to exemplary embodiments, it will be understood by those skilled in the art that various changes and modifications may be made without departing from the spirit and scope of the invention. Therefore, the invention is not limited to the particular embodiments disclosed as the best mode contemplated for carrying out this invention, but the invention will include all embodiments falling within the scope of the appended claims.

What is claimed is:

1. An organosilicon porous zeolite, wherein the organosilicon porous zeolite has the following composition on molar basis: (1/n)Al$_2$O$_3$:SiO$_{(2-m/2)}$:mR:xM, wherein n=5 to 1000, m=0.001 to 1, x=0.005 to 2, R is at least one selected from the group consisting of alkyl, alkenyl and phenyl and connected to a silicon atom in the framework of the zeolite, and M is an organic amine templating agent, and wherein a solid Si$^{29}$NMR spectrum of the organosilicon porous zeolite has at least one Si$^{29}$ nuclear magnetic resonance peak in the range of from −80 to +50 ppm.

2. The organosilicon porous zeolite according to claim 1, wherein an X-ray diffraction pattern of the organosilicon porous zeolite exhibits diffraction peaks corresponding to d-spacing of 12.4±0.2, 11.0±0.3, 9.3±0.3, 6.8±0.2, 6.1±0.2, 5.5±0.2, 4.4±0.2, 4.0±0.2 and 3.4±0.1 Å.

3. The organosilicon porous zeolite according to claim 1, wherein n is in a range of from 10 to 250, m is in a range of from 0.01 to 0.8, and x is in a range of from 0.01 to 1.

4. The organosilicon porous zeolite according to claim 3, wherein n is in a range of from 10 to 150, m is in a range of from 0.02 to 0.5, and x is in a range of from 0.02 to 0.5.

5. The organosilicon porous zeolite according to claim 1, wherein R is at least one selected from the group consisting of $C_1$-$C_8$ alkyl, $C_2$-$C_{10}$ alkenyl and phenyl.

6. The organosilicon porous zeolite according to claim 5, wherein R is at least one selected from the group consisting of methyl, ethyl, vinyl, and phenyl.

7. A process for preparing the organosilicon porous zeolite according to claim 1, comprising:
   a) mixing a source of organic silicon, a source of inorganic silicon, an aluminum source, an alkali, an organic amine templating agent and water to form a reaction mixture, wherein the reaction mixture has a composition in terms of molar ratios falling within the following ranges: $SiO_2/Al_2O_3$=5 to 1000, the source of organic silicon/$SiO_2$=0.001 to 1, $OH^-/SiO_2$=0.01 to 5.0, $H_2O/SiO_2$=5 to 100, and the organic amine/$SiO_2$=0.01 to 2.0, wherein $SiO_2$ represents the source of inorganic silicon in terms of $SiO_2$; and
   b) allowing the reaction mixture to react at a temperature of from 90 to 200° C. for 1 to 100 hours to form a crystalline product, and
   c) recovering the crystalline product obtained from step b), washing it with water and drying, to give the organosilicon porous zeolite.

8. The process according to claim 7, wherein the source of inorganic silicon is at least one selected from the group consisting of silica sols, solid silica, silica gels, silicic acid esters, diatomite and water glass; the source of organic silicon is at least one selected from the group consisting of halosilanes, silazanes and alkoxy silanes; the aluminum source is at least one selected from the group consisting of sodium aluminate, sodium metaaluminate, aluminum sulfate, aluminum nitrate, aluminum trichloride, aluminum hydroxide, aluminum oxide, kaolin and montmorillonite; the alkali is at least one selected from the group consisting of lithium hydroxide, sodium hydroxide, potassium hydroxide, rubidium hydroxide, and cesium hydroxide; the organic amine is at least one selected from the group consisting of ethylenediamine, hexamethylenediamine, cyclohexylamine, hexamethylene imine, heptamethylene imine, pyridine, hexahydropyridine, butylamine, hexylamine, octylamine, quinamine, dodecylamine, hexadecylamine, and octadecylamine.

9. The process according to claim 8, wherein the halosilanes include trimethylsilyl chloride, dimethylsilyl dichloride, triethylsilyl chloride, diethylsilyl dichloride, dimethylsilyl monochloride monobromide, ethyldimethylsilyl chloride, butyldimethylsilyl chloride, dimethylphenylsilyl chloride, dimethylisopropylsilyl chloride, tert-butyldimethylsilyl chloride, dimethyloctadecylsilyl chloride, methyl phenyl vinylsilyl chloride, vinylsilyl trichloride, divinylsilyl dichloride and diphenylsilyl dichloride; the silazanes include hexamethyldisilazane, heptamethyldisilazane, tetramethyldisilazane, divinyl tetramethyldisilazane, and diphenyl tetramethyldisilazane; and the alkoxy silanes include trimethylethoxysilane, dimethyldiethoxysilane, trimethylmethoxysilane, dimethyldimethyoxysilane, phenyltrimethoxysilane, and diphenyldiethoxysilane.

10. The process according to claim 7, wherein the reaction mixture has a composition in terms of molar ratios falling within the following ranges: $SiO_2/Al_2O_3$=10 to 250, the source of organic silicon/$SiO_2$=0.005 to 0.5, $OH^-/SiO_2$=0.05 to 1.0, $H_2O/SiO_2$=10 to 80, and the organic amine/$SiO_2$=0.05 to 1.0, wherein $SiO_2$ represents the source of inorganic silicon in terms of $SiO_2$.

11. The process according to claim 7, wherein the reaction temperature for crystallization is in a range of from 100 to 180° C., and reaction time for crystallization is in a range of from 2 to 60 hours.

12. The process according to claim 7, further comprising aging the reaction mixture at a temperature of from 10 to 80° C. for 2 to 100 hours prior to the crystallization reaction.

13. A catalyst comprised of the organosilicon porous zeolite according to claim 1.

14. An adsorbent comprising the organosilicon porous zeolite according to claim 1.

* * * * *